United States Patent
Pozo et al.

(10) Patent No.: US 9,873,731 B2
(45) Date of Patent: Jan. 23, 2018

(54) METHOD FOR INCREASING MILK PRODUCTION BY RUMINANTS

(71) Applicant: The Lauridsen Group, Inc., Ankeny, IA (US)

(72) Inventors: Francisco Javier Polo Pozo, Barbera del Valles (ES); Joy M. Campbell, Ames, IA (US); Louis E. Russell, Ankeny, IA (US); Alejandro Bach Ariza, Ankeny, IA (US)

(73) Assignee: The Lauridsen Group Incorporated, Ankeny, IA (US)

( * ) Notice: Subject to any disclaimer, the term of this patent is extended or adjusted under 35 U.S.C. 154(b) by 0 days.

(21) Appl. No.: 14/853,696

(22) Filed: Sep. 14, 2015

(65) Prior Publication Data

US 2016/0165922 A1   Jun. 16, 2016

Related U.S. Application Data

(60) Provisional application No. 62/173,791, filed on Jun. 10, 2015, provisional application No. 62/050,671, filed on Sep. 15, 2014.

(51) Int. Cl.
| | |
|---|---|
| A61K 35/16 | (2015.01) |
| C07K 16/00 | (2006.01) |
| C07K 16/06 | (2006.01) |
| A23K 1/04 | (2006.01) |
| A23K 10/24 | (2016.01) |
| A23K 20/147 | (2016.01) |
| A23K 50/10 | (2016.01) |

(52) U.S. Cl.
CPC ............... *C07K 16/00* (2013.01); *A23K 1/04* (2013.01); *A23K 10/24* (2016.05); *A23K 20/147* (2016.05); *A23K 50/10* (2016.05); *A61K 35/16* (2013.01); *C07K 16/06* (2013.01)

(58) Field of Classification Search
CPC .. A61K 2300/00; C07K 16/00; A23K 20/147; A23K 50/10
See application file for complete search history.

(56) References Cited

U.S. PATENT DOCUMENTS

| | | | |
|---|---|---|---|
| 6,004,576 A | 12/1999 | Weaver et al. | |
| 2006/0130768 A1* | 6/2006 | Crenshaw | A01K 29/00 119/51.01 |
| 2008/0112948 A1* | 5/2008 | Weaver | A23K 1/184 424/130.1 |
| 2013/0095093 A1 | 4/2013 | Campbell et al. | |

OTHER PUBLICATIONS

Fruge, E.D. et al. Effects of dietary spray-dried plasma protein on sow productivity during lactation. Journal of Animal Science, 2009, vol. 87, No. 3, p. 960-964.*

Clark, J. H., T. H. Klusmeyer, and M.A. Cameron. 1992. Microbial protein synthesis and flows of nitrogen fractions to the duodenum of dairy cows. J. Dairy Sci. 75:2304-2323.
Coffey, R. D., and Cromwell G. L. 2001. Use of spray-dried animal plasma in diets for weanling pigs. Pig News Info. 22:39N-48N.
Crenshaw et al., 2007. Lactation feed disappearance and wean to estrus interval for sows fed spray-dried plasma. J. Anim. Sci. 85:3442-3453.
Crenshaw et al., 2008. Effect of spray-dried plasma in diets fed to lactating sows on litter weight at weaning and subsequent farrowing rate. Proc. Allen D. Leman Swine Conf., Univ. MN, St. Paul, MN, p. 47.
Crenshaw et al., 2010. Effect of spray-dried plasma fed during gestation on pig performance at weaning. Proc. Allen D. Leman Swine Conf. Recent Res. Suppl., Univ. MN, St. Paul, MN, p. 193.
Santos, F.A.P., J. T. Huber, C. B. Theurer, R. S. Swingle, J.M. Simas, K. H. Chen, and P. Yu. 1998. Milk yield and composition of lactating cows fed steam-flaked sorghum and graded levels of ruminally degradable protein. J. Dairy Sci. 81 :215-220.
Santos, F.A.P, Santos, J.E.P., Theurer C.B., and J.T. Huber. 1998. Effects of rumen undegradable protein on dairy cow performance: a 12-year literature review. J Dairy Sci 81:3182-3213.
Schor, A and G. A. Gagliostro. 2001. Undegradable protein supplementation to early-lactation dairy cows in grazing conditions J. Dairy Sci. 84:1597-1606.
Song et al., 2012a. Effect of graded levels of dietary spray-dried plasma on pregnancy rate of mated female mice under transport stress as a model for stressed sows. J. Anim. Sci. vol. 90 (E-Suppl. 2):112.
Spencer et al., 2003. Early weaning to reduce tissue mobilization in lactating sows and milk supplementation to enhance pig weaning weight during extreme heat stress. J. Anim. Sci. 81:2041-2052.
Torrallardona, D. 2010. Spray-dried animal plasma as an alternative to antibiotics in weanling pigs: a review. Asian-Aust. J. Anim. Sci. 32:131-148. 1-1.
Van Dijk, A. J., Everts H., Nabuurs M. J. A., Margry R. J.C. F., and Beynen A. C. 2001. Growth performance of weanling pigs fed spray-dried animal plasma: a review. Livest. Prod. Sci. 68:263-274.
Van Iersel et al., 2011. Effect of spray-dried plasma in lactation feed on pig survival and litter weight at a commercial farm in Italy. Proc. Allen D. Leman Swine Conf., Recent Research Reports, College of Veterinary Medicine, Univ. MN, St. Paul, MN, vol. 38, p. 281.
Virtanen, A. I. 1966. Milk production of cows on protein-free feeds. Science 153:1603-1608.
Chandler P. T. 1991. Quantitative and qualitative characteristics of protein sources and interrelationships with energy. Virginia Dairyman 12: I 0, 12.
Dohoo et al., Can. J. Vet. Med., 67, 241-264 (2003).
Safranski et al., 2010. Physiological and reproductive response to periparturient heat stress in sows. J. Anim. Sci. 89 (E-Suppl. 2):70.
Schingoethe, D. J. 1991. Protein quality and amino acid supplementation in dairy cattle. pp. 101-106 in Proc. Southwest Nutr. Manage. Conf., Tempe, AZ. Dep. Anim. Sci., Univ .Arizona, Tucson.
Schwab, C. G. 1994. Optimizing amino acid nutrition for optimum yields of milk and milk protein. pp. 114-129 in Proc. Southwest Nutr. Manage. Conf., Phoenix, AZ. Dep. Anim. Sci., Univ. Arizona, Tucson.

(Continued)

*Primary Examiner* — Robert Landsman
*Assistant Examiner* — Bruce D Hissong
(74) *Attorney, Agent, or Firm* — Buchanan Ingersoll & Rooney PC

(57) ABSTRACT

This invention relates to the administration of an animal immunoglobulin source to mammals such as dairy cattle to improve milk production without negatively affecting reproductive parameters.

13 Claims, 8 Drawing Sheets

(56) References Cited

OTHER PUBLICATIONS

Song et al., 2012b. Effect of graded levels of dietary spray-dried plasma on growth and fetal characteristics of pregnant mice as a model for sows. J. Anim. Sci. vol. 90 (E-Suppl. 2):112.

Borg, B. S., Campbell J.M., Koehnk H., Russell L. E., Thomson D. U., and Weaver E. M. 1999. Effects of a water soluble plasma protein product on weanling pig performance and health with and without *Escherichia coli* challenge. Proceedings of Allen D. Leman Swine Conference 26:23-24. Li.

* cited by examiner

METHOD FOR INCREASING MILK PRODUCTION BY RUMINANTS

CROSS-REFERENCE TO RELATED APPLICATIONS

This application claims priority from U.S. Provisional Application No. 62/173,791, filed Jun. 10, 2015 and U.S. Provisional Application No. 62/050,671 filed Sep. 15, 2014, both of which are incorporated by reference herein in their entireties.

BACKGROUND OF THE INVENTION

Proteins have a variety of functions within the body that include stimulatory, catalytic, transport, structural and molecular sequestering activities. The definition of functional proteins varies among different scientific disciplines. Functional proteins can be defined as proteins that when fed to animals improve animal performance and well-being beyond what can be explained solely by our understanding of nutrition.

Spray-dried plasma (SDP) is a functional protein source that has considerable peer reviewed research describing its beneficial impact on immune response and barrier function when fed to animals. Spray-dried plasma consists primarily of albumin, globulins, fibrinogen along with lesser quantities of other proteins or peptides. As used herein the term "plasma" shall include the plasma portion of blood as well as any of the protein components which may be further purified therefrom. Purifications of these components from plasma are methods known and commonly practiced by those of skill in the art.

Numerous studies involving challenge or natural infection with pathogenic bacteria, viruses, or protozoa have reported reduced mortality and/or improved health indices in a variety of species (swine, calves, poultry, and shrimp) fed diets containing spray-dried plasma proteins. Although spray-dried plasma contains globulin protein, (Borg et al., 2002) antibody neutralization of antigens in the gut lumen does not fully explain the improvements noted in animals fed plasma proteins.

Spray-dried plasma proteins are used extensively in nursery pig feed to enhance feed intake, growth, and feed efficiency during the post-weaning period. Scientific reviews of published research clearly show that addition of spray-dried plasma to pig diets at weaning increases feed intake, growth rate, and improves feed efficiency (Coffey and Cromwell, 2001; Van Dijk, 2001; Torrallardona, 2010).

The nutrition provided by SDP in gestating sow feed can support litter performance (Crenshaw et al., 2010). Primiparous sows provided a gestation diet containing SDP from day 14 of pregnancy to farrowing had heavier pigs at birth, fewer pigs weighing less than 1 kg at birth, and both primiparous and multiparous sows had pigs that were heavier at 18 d of age compared to sows provided a diet without SDP. Similar results were observed in a pregnant mouse model of transport stress in which mice provided nutrition from diets containing SDP had increased pregnancy rate along with larger litter size and heavier average fetal weight near the end of pregnancy compared to mice provided a diet without SDP (Song et al., 2012 a,b).

Heat stress reduces feed intake of lactating sows and pig weight at weaning (Spencer et al., 2003; Safranski et al., 2010). Several studies reported that the nutrition provided by SDP in lactation diets support sow and litter performance, particularly if fed during summer months (Crenshaw et al., 2007, 2008; Van Iersel et al., 2011). In these studies SDP in lactation diets contributed to improved pig survival to weaning, heavier litters at weaning, greater feed intake by young sows, reduced wean to estrus interval of primiparous sows, and increased farrowing rate of sows to the next lactation compared to a lactation diet without SDP.

Collectively, these studies demonstrate that the enhanced nutrition provided by SDP in diets support sow productivity indices, including pig survival and pig weight gain to weaning, particularly during periods of stress associated with summer heat.

SUMMARY OF THE INVENTION

The invention provides a method for increasing milk production in mammals, such as ruminant animals, e.g., cattle (dairy cows), goats, sheep, deer, yaks and camels. The present method comprises the administration of an effective amount of an immunoglobulin source derived from the blood plasma or serum of an animal such as a pig, bovine, ovine, avian or goat. Therefore, the term "immunoglobulin source" as used herein includes dried animal plasma, dried animal serum, an immunoglobulin concentrate derived therefrom, preferably dried, or any combination thereof. The immunoglobulin source is nonspecific and isolation of useful immunoglobulin sources from blood can be accomplished by methods known and commonly practiced by those of skill in the art. The present method is useful to improve milk production in dairy cattle and other milk-producing ruminant animals without affecting reproductive parameters. The animal plasma, serum or immunoglobulin fractions thereof and mixtures may be administered in either granular or powder form or in suspension or solution. See, e.g., Weaver et al., U.S. Pat. No. 6,004,576 and U.S. patent application Ser. No. 13/463,127, filed May 3, 2012. In one embodiment of the present method, the immunoglobulin source is powdered or granular and consists essentially of a mixture of dried animal (non-human) plasma (SDP) in a concentration between about 0.05-1% to about 98%, dried animal serum in a concentration between 1 to 50% and dried animal immunoglobulin concentrate in a concentration between 1 to 25%. Percentages are wt-% unless otherwise indicated.

The term "immunoglobulin source" does not include whole blood or blood meal.

DETAILED DESCRIPTION OF THE INVENTION

Figure 1:
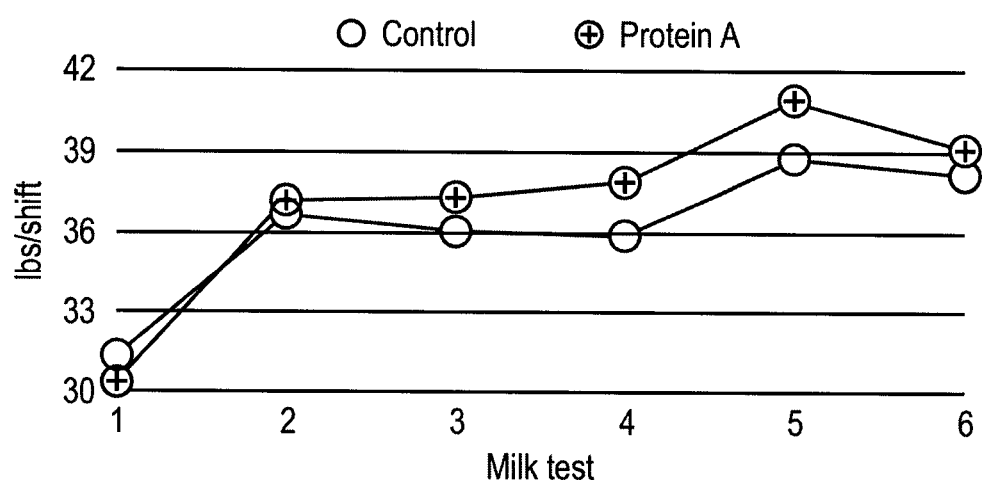
FIG. 1 is a graph plotting pounds of milk per shift vs. milk test periods (mos.). O=control diet; ⊗=SDP (Protein A) diet.

For many years, crude protein (CP) content was used in formulating diets for lactating dairy cows because little was known of the response to dietary protein of varying quality. Many researchers postulated that the high quality microbial protein synthesized in the rumen would complement deficiencies in the quality of dietary protein that escaped rumen fermentation (Schingoethe, 1991). Research conducted in the 1960s (Virtanen, 1966) showed that the rumen was capable of supplying all of the protein required by cows producing up to 4,500 kg of milk per lactation. However, milk yield per cow in the US has more than doubled during the last 30 yr, and the general concern currently is for cows yielding from 9,000 to 14,000 kg of milk annually. For these high yielding cows, microbial protein synthesis supplies a decreasing proportion of the required protein, and significant amounts of dietary protein must escape rumen degradation in order to meet protein needs (Santos et al., 1998a).

Based on the rumen degradable protein (RDP)-rumen undegradable protein (RUP) model, increased milk yields are usually expected from substituting a high RDP with a high RUP source of supplemental protein. However, in the review of Santos et al. (1998b), many studies are cited in which soybean meal (SBM; the most commonly used protein supplement in the US) replacement by a high RUP source resulted in a general lack of response in milk yield. Possible reasons for this lack of response to increased RUP are 1) microbial synthesis in the rumen decreased (Clark et al., 1992; Schingoethe, 1991; Schwab, 1994), 2) the RUP source had a poor essential amino acid profile (Chandler, 1991; Schingoethe, 1991; Schwab, 1994), 3) RUP sources in the small intestine (SI) had low digestibility (Schingoethe, 1991; Schwab, 1994), and 4) control diets already were sufficiently high in RUP (National Research Council, 1985; 1989).

Common protein supplements that are high in RUP and are used in ruminant diets in the US are fish meal (FM), meat and bone meal (MBM), feather meal, blood meal (BM), corn gluten meal (CGM), distillers dried grains (DDG), DDG with solubles (DDGS), brewers dried grains (BDG), and brewers wet grains (BWG).

In the compilation of Santos et al. (1998b), they reviewed 108 studies published between 1985 and 1997. In 29 comparisons from 15 metabolism trials, soybean meal was replaced by high amounts of RUP as a supplement; the benefits were not consistently observed for flow to the duodenum, essential amino acids, or lysine and methionine. High RUP diets resulted in decreased microbial protein synthesis in 76% of the comparisons. In 127 comparisons from 88 lactation trials, researchers studied the effects of replacing soybean meal with high RUP sources, such as heated and chemically treated soybean meal, corn gluten meal, distillers grains, brewers grains, blood meal, meat and bone meal, feather meal, or blends of these sources. Milk yield was significantly higher in only 17% of the comparisons. Fish meal and treated soybean meal accounted for most of the positive effects on milk yield from RUP; corn gluten meal resulted in mostly negative results. The percentage of fat in milk was depressed more by fish meal than by other RUP sources. Protein percentage was decreased in 28 comparisons and increased in only 6 comparisons, probably reflecting the decrease in microbial protein synthesis, as was observed for diets high in RUP. The data strongly suggest that increased RUP per se in dairy cow diets, which often results in a decrease in RDP and a change in absorbed amino acid profiles, does not consistently improve lactation performance.

In another publication by Schor and Gagliostro (2001) the authors determined the production responses to RUP feeding during grazing conditions. They fed 18 multiparous Holstein cows concentrates containing either SBM or BM during the first 8 week of lactation. On a dry matter (DM) basis, concentrates contained SBM (33%) or BM (13%), corn grain (64 and 84% for SBM and BM, respectively) and a mineral-vitamin complex (3%). Concentrates were offered at a rate of 6.6 kg/d per cow and herbage allowance averaged 31 kg/d of DM per cow. The BM reduced rumen ammonia-N levels and had no effect on rumen pH and molar volatile fatty acid concentration. The degradable fraction (63.59 vs. 22.46%) and the rate of disappearance of the CP (9.68 vs. 1.69%/h) were greater for the SBM compared with the BM concentrate. Cows fed the BM concentrate produced more milk (29.3 vs. 24.9 kg/d) and more milk protein (0.85 vs. 0.74 kg/d) than did those fed the SBM concentrate. Milk fat yield and percentages of milk fat, lactose and protein were not affected. Forage dry matter intake was increased by BM (17.19 vs. 13.17 kg/d per cow). Results in this study indicated that a concentrate with a high RUP content increased milk and milk protein yields when spring pasture was the sole forage. The highest milk yield was more likely caused by increased DM than by enhanced body lipid mobilization.

Another Common treatment to improve milk production in some countries is the injection of cows with recombinant bovine somatotropin (rBST), a recombinant hormone similar to the peptide hormone produced in the cow's pituitary gland. Two meta-analyses have been published by Dohoo et al. (2003). Their findings indicated an average increase in milk output ranging from 11% to 16%, a nearly 25% increase in the risk of clinical mastitis, a 40% reduction in fertility and a 55% increased risk of developing clinical signs of lameness. The same studies reported a decrease in body condition score for cows treated with rBST even through there was an increase in their dry matter intake.

According to an embodiment of the present method, blood plasma obtained from animal sources is powdered or granulated and fed with other feed ingredients to mammals such as dairy cows. Any mammal in which it is desirable to increase milk production can be fed the composition according to the invention, this includes but is not limited to cows, goats, sheep, camels, yaks pigs or horses. The plasma is obtained by collecting blood from animals. The blood from any red blooded animal (porcine, bovine, ovine, equine, avian sp.) can be used to practice the invention. In a preferred embodiment the animal is a livestock animal which is slaughtered for its meat product. The blood, which is traditionally discarded or dried and processed as blood meal, may then be used for preparation of the compositions and implementation of methods of the invention. In a most preferred embodiment the blood is collected from pigs or cattle.

Generally, according to the invention, blood is collected, preferably at slaughter plants. In one embodiment, the blood may be held in a circulating stainless steel tank with anticoagulants such as sodium citrate or sodium phosphate to prevent clotting. Prevention of clotting is not essential to the invention as similar effects can be obtained with clot-removed serum or defibrinated plasma. Typically, the whole blood is then separated, preferably by centrifugation, although any other separation method may be used, into two parts, the cellular material (red corpuscles, white corpuscles, platelets, and other circulating precursor cells of the previous categories of cells) and plasma. Plasma is composed of about 55-60% albumin, 25-40% globulin, 10% fibrinogen, and other proteins. After separation, the plasma may be cooled to retard growth of bacteria and stored in an insulated tank until ready to dry.

Plasma and/or the purified components of plasma, may then be further concentrated (by membrane filtration). The concentrated product is next dried, preferably by spray-drying to form a beige powdery substance (SDP). Spray-drying should occur at temperatures low enough to prevent the complete denaturation of proteins but high enough to reduce bacterial and viral contamination. Traditionally, a drier inlet temperature of approximately 375° to 400° F. and an outlet temperature from the drier of 180-200° F. will accomplish this objective. The resulting powdery substance will have a particle size of about 5 to about 400 microns. The powder then is compacted or compressed (around 1200 to 1400 psi), ground and optionally may be screened or otherwise separated by size to increase homogeneity. The resulting particle size is at least about 50 microns. Preferably the size is greater than about 100 microns but less than about 2000 microns in diameter. This size is sufficient so that the granulated particles are able to pass from the stomach to the small intestine without breakdown into smaller particles by the stomach. In addition to granulation, many methods, such as pelleting, wet or dry agglomeration, prilling, and fluid-bed drying, may be used to increase the particle size and density of dried plasma and/or its component proteins without causing significant denaturation and are intended to be included within the scope of the invention. The granulation of plasma results in a bulk density increase of from about 32 pounds per cubic foot in powder form to about 50 pounds per cubic foot in granular form. The resulting granular substance may then be combined with other feed ingredients for any desired feeding regime or may be blended with a feed ingredient and the blend granulated. The diets consist primarily of processed grains (corn, wheat, barley, rice, etc.), alfalfa, oats, rolled oats, corn silage, haylage or hay blends, wheat bran, soybean meal, cottonseed meal or whole cottonseed, gelatinized starches, milk products (dried skim milk, dried whey, lactose, dried whey protein concentrate, casein, etc.), molasses, sugars (dextrose, glucose, sucrose), fats and/or oils (bypass fat sources, lard, grease, vegetable oils, tallow, etc.), urea, animal proteins (fishmeal, bloodmeal, meat meal, etc.), and refined, extruded soybeans (soy protein isolate, soy protein concentrate). The amount of the granulated substance administered (fed) is an amount at which the improved effects occur. The granulated substance preferably comprises from greater than 0, e.g., about 0.1 wt-% to about 6.0 to about 9.0 wt-% up to about 10-15% by weight of the total mixed ration (TMR), preferably about 0.1-1 to about 5%, e.g., about 0.25-4 wt-%, about 1-5 wt-% or about 2-3 wt-% by weight of the TMR. The TMR includes the forages injested by the animal. The dried plasma powder or granules contemplated for use in this method comprise high levels of amino acids.

Chemical and other properties of dried plasma include about 60-85% protein, 9% moisture, 5-20% ash, 2% fat, 50.0 ppm iron, 0.15% calcium, 1.50% chloride; 1.7% phosphorous, 0.09% potassium, aqueous solubility 88%.

As used herein with reference to the composition of the invention, the immunoglobulin source is also intended to include an immunoglobulin concentrate or fraction thereof purified from animal sources including blood, egg, or milk which retains the Fc region of the immunoglobulin molecule. Immunoglobulin concentrates may be obtained according to any of a number of methods available in the art. Comparison of four purification methods for the production of immunoglobulins from eggs laid by hens immunized with an enterotoxigenic *E. coli* strain. *Journal of Immunological Methods* 160:207-214; Steinbuch, M. and R. Audran. 1969. The isolation of IgG from mammalian sera with the aid of caprylic acid. *Archives of Biochemistry and Biophysics* 134:279-284; Lee, Y., T. Aishima, S. Nakai, and J. S. Sim. 1987. Optimization for selective fractionation of bovine blood plasma proteins using polyethylene glycol). *Journal of Agricultural and Food Chemistry* 35:958-962; Polson, A., G. M. Potgieter, J. F. Langier, G. E. F. Mears, and F. J. Toubert. 1964. *Biochem. Biophys. Acta.* 82:463-475.

Animal plasma from which immunoglobulin or other plasma fractions may be isolated include pig, bovine, ovine, poultry, equine, or goat plasma. Additionally, applicants have identified that cross species sources of the immunoglobulins still provide the effects of the invention.

The immunoglobulin concentrate can be derived from animal blood. The source of the blood can be from any animal that has blood which includes plasma and immunoglobulins. For convenience, blood from beef, pork, and poultry processing plants is preferred. Anticoagulant is added to whole blood and then the blood is centrifuged to separate the plasma. Any anticoagulant may be used for this purpose, including sodium citrate and heparin. Persons skilled in the art can readily recognize such anticoagulants. Calcium is then added to the plasma to promote clotting, the conversion of fibrinogen to fibrin; however other methods are acceptable. This mixture is then centrifuged to remove the fibrin portion.

Once the fibrin is removed from plasma resulting in serum, the serum can be dried and used as a principal source of immunoglobulin. Alternatively, one could also inactivate this portion of the clotting mechanism using various anticoagulants.

The defibrinated plasma is next treated with an amount of salt compound or polymer sufficient to precipitate the albumin or immunoglobulin fraction of the plasma. Examples of phosphate compounds which may be used for this purpose include all polyphosphates, including sodium hexametaphosphate and potassium polyphosphate. The immunoglobulin concentrate may also be isolated through the addition of polyethylene glycol, ammonium sulfate, or other fractionation methods, i.e., by using caprylic acid.

Following the addition of the phosphate compound, the pH of the plasma solution is lowered to stabilize the albumin precipitate. The pH should not be lowered below 3.5, as this will cause the proteins in the plasma to become damaged. Any type of acid can be used for this purpose, so long as it is compatible with the plasma solution. Persons skilled in the art can readily ascertain such acids. Examples of suitable acids are HCl, acetic acid, $H_2SO_4$, citric acid, and $H_2PO_4$. The acid is added in an amount sufficient to lower the pH of the plasma to the designated range. Generally, this amount will range from a ratio of about 1:4 to 1:2 acid to plasma. The plasma is then centrifuged to separate the immunoglobulin fraction from the albumin fraction.

The next step in the process is to raise the pH of the immunoglobulin fraction with a base until it is no longer corrosive to separation equipment. Acceptable bases for this purpose include NaOH, KOH, and other alkaline bases. Such bases are readily ascertainable by those skilled in the art. The pH of the globulin fraction is raised until it is within a non-corrosive range which will generally be between 5.0 and 9.0. The immunoglobulin fraction is then preferably microfiltered to remove any bacteria that may be present.

The final immunoglobulin concentrate can optionally be spray-dried into a powder. The powder allows for easier packaging and the product remains stable for a longer period of time than the raw globulin concentrate in liquid or frozen form. The immunoglobulin concentrate powder has been found to contain approximately 30-60% IgG. In certain embodiments, theilmmonuglobulin concentrate powder contains at least 35-40 wt-% IgG up to about 50-55 wt-% IgG Animal plasma proteins comprising immunoglobulin contents of over about 20-90 wt-%, e.g., over 90 wt-% are described in published European patent application 1044690 A1.

In other embodiments, the immunoglobulin concentrae powder additionally contains about 1-2 to about 20-25 wt-% IgA.

Concentrates of the product can be obtained by spray drying, lyophylization, or any other drying method, and the concentrates may be used in their liquid or frozen form. The active ingredient may also be microencapsulated, protecting and stabilizing from high temperature, oxidants, pH-like humidity, etc.

The spray-dried plasma and/or serum derived immunoglobulin concentrate(s) is preferably fed to ruminant animals prior to their giving birth and for a period of time post-partum, e.g. for about 10-50 days before delivery, e.g., 15-35 days before calving and for about 50-500 days post-partum, e.g., about 75-300 DIM. The amount of concentrates injested per day will vary depending on the size of the animal, e.g., in bovines it will be about 100-750 g/day, e.g., about 150-500 g/day, along with the other components of their ration. The animals may ingest about 100-300 g/day of the concentrate(s) pre-delivery and about 300-500 g/day post-partum.

As can be observed in Example 1 below, dairy cattle were fed granular SDP from about 30 days before calving until 100 days in milk (DIM) after delivery of a calf and an unexpected increase in milk production in the third month with average 75 DIM observed that was quantified in approximately 2 lb more milk per shift or about 6 lbs more milk per day (these cows were milked three times per day) in comparison with a control TMR containing blood meal as RUP or by-pass protein at a similar inclusion level. What was unexpected was the degree of improvement (around 6 lb milk/day or 2.7 kg milk/day) taking in consideration that the control diet already contained a very well recognized by-pass protein like blood meal and the fact that the inclusion level used in the administration of the SDP was only 200 or 450 g of supplement per day for the pre-calving and post-calving supplementation period. The study of Schor and Gagliostro (2001) indicated an improvement of milk production in calves supplemented with blood meal of similar values but the blood meal supplement was added at 6.6 kg per day per cow which was between 15 to 33 times higher than the amount of functional protein supplement fed in our study. Also they were comparing the effect of blood meal supplementation as RUP versus SBM which does not have a by-pass effect and in the study herein below compared SDP versus BM.

Also supplementation with SDP did not have a negative effect on reproductive performance. It is well known that dramatic increases in milk production has a negative effect on reproductive performance and body condition of cows, however, unexpectedly, in our study, no reduction in pregnancy rate, overall conception rate, or time to new pregnancy was observed. Also cows supplemented with SDP maintained a similar body condition score (BCS) between the two groups of cows at all periods of the study.

Another important observation was the fact that the amount of fat in milk was greater (P<0.05) in the group of cows supplemented with SDP (3.55%) than in the Control group (3.47%).

Example 1

Objectives

To determine the impact of granular spray-dried bovine plasma (SDP, Appetein®, APC, Inc., Ankeny, Iowa, named in this example as Protein A) supplementation at the level of about 0.5-2 wt-% of dry matter intake (feed) during the immediate pre- and post-parturient periods on early lactation reproductive performance and milk production.

Materials & Methods

A total of 998 dairy cows from one large herd in the Western US were blocked on the basis of parity and randomly assigned to one of two treatment groups at calving:

Group 1 (T or Trial Code=1) received a total mixed ration (TMR) supplying 200 or 400 g/d of protein A before or after calving respectively (n=495) as shown on Tables A and B.

Group 0 (C or Control Code=0) served as a control group, receiving the same TMR but control protein (blood meal) supplementation. As shown on Tables A and B. This TMR contained blood meal and thus rations were easily balanced to achieve isonitrogenous levels with the treated group (n=503).

Rations were fed for approximately 21 d before calving, and for some cows the treatment was continued up to 200 d post-partum.

TABLE A

RATION FOR CLOSE-UP WITH CONTROL AND PROTEIN A

| Close Up Diets Ingredient | Protein A lb/d | Control lb/d |
|---|---|---|
| Alfalfa | 13.3 | 13.3 |
| Ground corn | 2.5 | 2.5 |
| Soybean meal | 1.4 | 1.4 |
| Corn silage | 36.52 | 36.52 |
| Protein A | 0.55* | |
| Blood meal | | 0.46 |
| Vitamin-mineral premix | 2 | 2 |
| SoyChlor (W.C. Coop.) | 1 | 1 |
| Whole cottonseed | 1.5 | 1.59 |
| Analyticals | | |
| Net energy, Mcal/lb | 0.65 | 0.65 |
| Crude Protein, % | 15.5 | 15.5 |
| RUP (% of crude protein) | 32 | 33 |
| Ether extract, % | 3.7 | 3.8 |
| Neutral detergent fiber, % | 37.1 | 37.8 |
| Lignin, % | 4.5 | 4.5 |
| NFC, %** | 36.4 | 36.4 |

TABLE A-continued

RATION FOR CLOSE-UP WITH CONTROL AND PROTEIN A

| Close Up Diets<br>Ingredient | Protein A<br>lb/d | Control<br>lb/d |
|---|---|---|
| Starch, % | 15.9 | 15.9 |
| Lysine:Methonine | 3:1 | 3.1 |

*249 g
**Non-fiber Carbohydrates

TABLE B

RATION FOR LACTATING PERIOD
WITH CONTROL AND PROTEIN A

| Lactation Diets<br>Ingredient | Protein A<br>lb/d | Control<br>lb/d |
|---|---|---|
| Molasses | 3 | 3 |
| High moisture corn | 15.32 | 15.32 |
| Hay Blend | 7.24 | 7.24 |
| Corn Silage | 50 | 50 |
| By pass fat | 0.9 | 0.9 |
| Whey | 8 | 8 |
| Tallow | 0.2 | 0.2 |
| Whole cottonseed | 5.11 | 5.11 |
| Protein A* | 0.88 | |
| Blood meal | | 0.75 |
| Palmit 80 | 0.31 | 0.31 |
| Soybean meal | 3.61 | 3.67 |
| SoyPlus ® (W.C. Coop) | 4.09 | 4.09 |
| Mineral-vitamin premix | 0.25 | 0.25 |
| Salt plain | 0.15 | 0.15 |
| Sodium bicarbonate | 0.12 | 0.12 |
| Buffer | 0.61 | 0.61 |
| Limestone | 0.36 | 0.36 |
| Magnesium Oxide | 0.05 | 0.05 |
| Biotin, 2% | 0.002 | 0.002 |
| Rumensin | 0.005 | 0.005 |
| Chromium Propionate | 0.004 | 0.004 |
| Metasmart (methionine source) | 0.082 | 0.082 |
| Yeast extract (Diamond V XPC) | 0.02 | 0.02 |
| Live yeast + MOS** | 0.018 | 0.018 |
| Analyticals | | |
| Net energy, Mcal/lb | 0.78 | 0.78 |
| Crude Protein, % | 17.6 | 17.6 |
| RUP (% of crude protein) | 37.8 | 38.4 |
| Ether extract, % | 6.8 | 6.8 |
| Neutral detergent fiber, % | 27.3 | 27.8 |
| Lignin, % | 2.5 | 2.5 |
| NFC, % | 41.7 | 41.7 |
| Starch, % | 24.6 | 24.7 |
| Lysine:Methonine | 3:1 | 3.:1 |

*399 g
**Mannanoligosaccharides

After calving, cows were placed in either a Control or a Treatment pen for 21 days. Each pen held about 140 cows. After that, they were moved into 4 pens of 320 cows each. Each cow wore a colored button ear tag consistent with the group assignment. Within treatment groups, cows were randomly assigned either treatment or control pens. Cows were retained in the fresh pen and monitored during the first 21 days in lactation. All cows were monitored for metabolic and infectious disease issues by on-farm staff during the immediate post-parturient period. Specific health events that were recorded and compared between groups included clinical hypocalcemia, retained fetal membranes, acute puerperal metritis, displaced abomasum, lameness, and clinical mastitis. Retained fetal membranes were defined as the presence of fetal membranes still visible at the vulva for >24 h after calving. Metritis was defined as the presence of a flaccid uterus containing fetid fluids, as characterized via rectal palpation, and the presence of a rectal temperature >39.7° C. in cows that were 2 to 14 days in lactation.

Following the fresh monitoring period, cows were randomly assigned into breeding pens and cows in each group continued to receive their respective dietary treatment. Cows continued to be monitored for metabolic and infectious disease thereafter.

Breeding management for first service consisted of a modified Pre-synch-Ovsynch timed AI protocol applied weekly beginning with an initial intramuscular injection of 500 µg cloprostenol of an analogue of PGF2α (Closprostenol sodium; Estrumate, Schering-Plough Animal Health Corp.) for all cows that were greater than about 44-50 DIM. An additional i.m. injection of PGF2α was given at 58-64 DIM. After the second injection of PGF2α, cows were bred. Breeding was based on estrus detection by direct visual examination and via tail chalking using paint sticks.

At 72-78 DIM, all cows not yet inseminated were enrolled into a CIDR-sync program and had a controlled internal drug release (CIDR) inserted vaginally and given an injection of 100 µg GnRH. In seven days, the CIDR was removed and 250 µg of PGF2α injected intramuscular. After 72 h, a second i.m. injection of 100 µg GnRH was given with breeding on appointment to follow in 72 h. This is a standard procedure used in the dairy industry worldwide. All inseminations were performed by one of three on-farm artificial insemination technicians using a blend of proven and young sire semen. The technician performing the artificial insemination was recorded and accounted for in the statistical analysis.

Following insemination, cows were examined daily for return to estrus. Cows not yet observed in estrus and re-inseminated were examined for pregnancy via palpation per rectum at 35-41 days post-insemination. Non-pregnant cows were re-enrolled into a 72-h Ovsynch program that followed the same schedule as the previously described, but without the use of CIDR. Cows observed in estrus at any time following the voluntary waiting period (60 d after calving) were inseminated and removed from their respective timed AI protocol. Cows determined pregnant by rectal palpation were verified pregnant again by rectal palpation at 70-76 d post insemination.

Measurements
  First, second and third service conception risk
  Impact on incidence of disease, especially metritis, but also mastitis (somatic cell count were determined monthly). Pregnancy loss between first diagnosis at 35-41 d following conception and confirmation at 70-77 days following conception.
  Milk production throughout 200 days in lactation. Not all cows were monitored at all times (only half of the cows were monitored at any given time due to a shortage of milk meters). Milk production was monitored on a monthly basis at one milking. There were, in total 387 cows in Control and 385 cows in Protein A.
  Post-partum disease
  Cows were body condition scored at calving, 14 and 30 days in milk.
  Blood samples were collected at 5 days after calving to determine concentration of beta-hydroxy butyric acid.

Data Recording

A member of the investigation team was responsible for randomization and allocation of cows into treatment or control groups. Lame cows were excluded from the study.

Specific health events such as retained fetal membranes, clinical hypocalcemia, metritis, pneumonia, and displaced abomasums were recorded by dairy staff into the on-farm computer program. Days in pre-fresh pen, calving dates, reproductive outcomes and culling information was collected from on-farm computer.

Data Processing and Statistical Analysis

All data were extracted from the farm computer and processed by animal. Out of the 1,008 cows initially enrolled, 10 were removed from the study because they became lame while dry (9 in the Control and 1 in the Protein A group). Then, out the 998 cows enrolled in the study, 50 had an abortion. These 50 cows (22 in Control and 28 in Protein A) were only included in the analysis to determine conception rate at first artificial insemination, and excluded for the rest of parameters (because an abortion would compromise fertility and milk production thereafter). Similarly, for milk data, there were 884 cows that were at least sampled once for milk production. But, those cows that were only sampled once, were removed from the analysis for milk production, thus milk results are based on 772 cows (387 in Control and 385 in Protein A).

Milk production and composition was analyzed using a mixed-effects model with repeated measures with the fixed effects of treatment, month and their 2-way interaction and days in milk as a covariate, and the random effect of sampling month and cow within treatment.

Reproductive data were analyzed using mixed-effects logistic regression analysis with treatment as a fixed effect and pen as a random effect.

Results

Overall, there were 3.2% cows with retained placenta in the Control group and 5.0% in the Protein A group (P=0.22). Similarly, there were no differences in the incidence of mastitis (P=0.47; 17.9 and 15.2% in Control and Protein A, respectively), metritis (P=0.19; 2.7 and 1.4% in Control and Protein A, respectively), displaced abomasums (P=0.42; 0.6 and 0.0% in Control and Protein A, respectively), or culling rate (P=0.90; 18.2 and 19.1% in Control and Protein A, respectively) and abortion rate (P=0.63; 4.5 and 5.6% in Control and Protein A, respectively). However, there was a tendency (P=0.07) for cows in the Protein A group to experience a greater incidence of lameness (38.0%) than those in Control (25.8%). There were, however, no differences (P=0.75) in the average days in milk at which cows became lame (114.3 and 112.6 for Control and Protein A cows, respectively).

Figure 2:
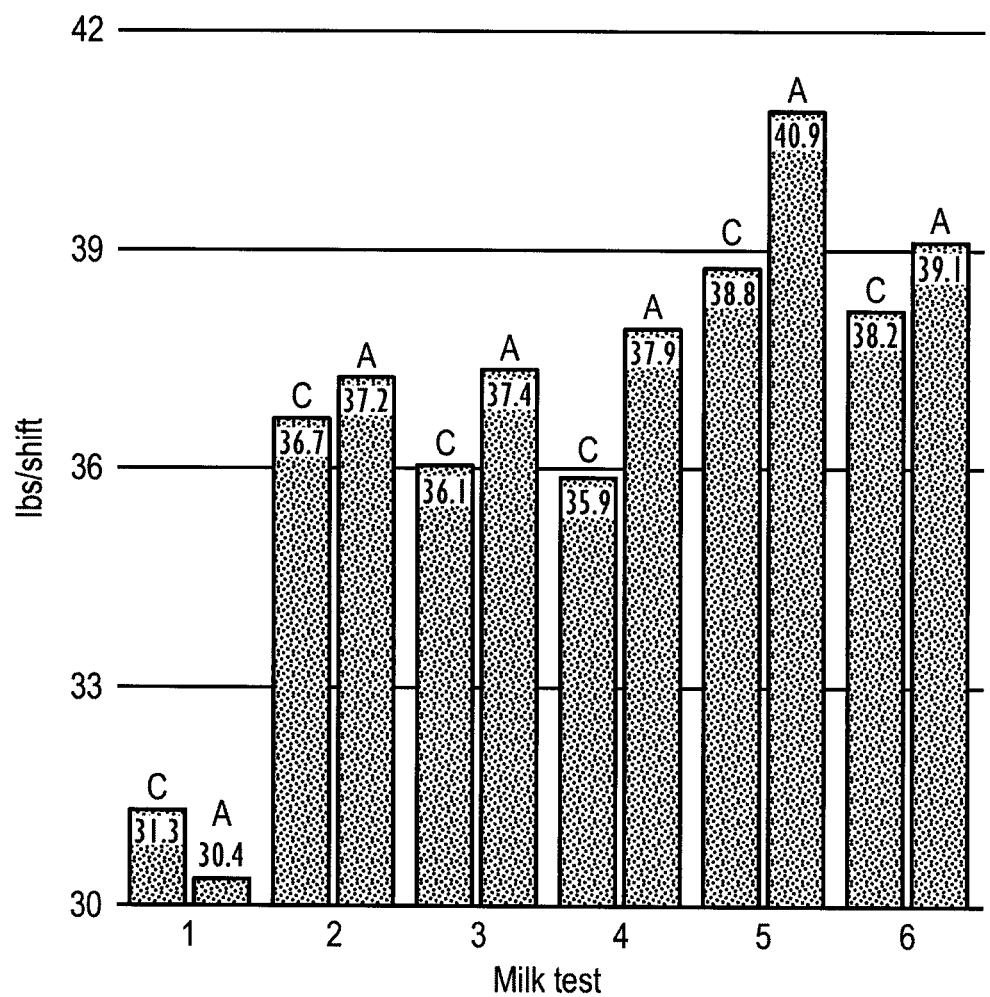
FIG. 2 is a bar graft plotting pounds of milk per shift vs. milk test periods (mos.). C=control; A=SDP (Protein A) diet.
Figure 6:
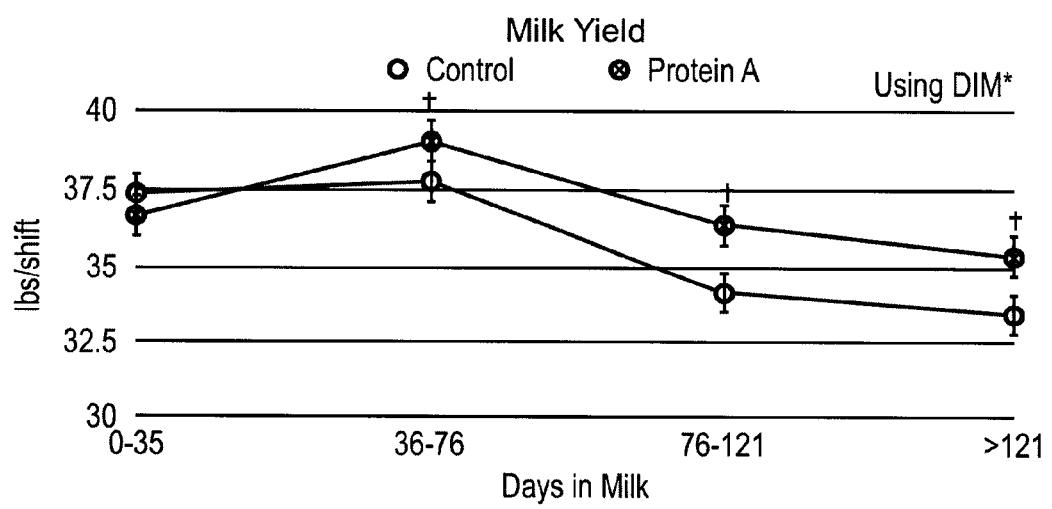
FIG. 6 is a graph plotting pounds of milk per shift vs. periods of days in milk. O=control diet; ⊗=SDP (Protein A) diet.

For the whole period, milk yield was greater (P<0.01) in Protein A (37.1 lbs/milking) than in Control cows (36.1 lbs/milking). Interestingly, there was an interaction (P<0.01) between treatment and time (FIG. 1). As can be observed in FIG. 1 at 3 months of supplementation or in FIG. 6 during 36-76 days in milk, there was a significant (P<0.05) increase in milk production in the cows supplemented with the protein A (37.5 lbs/milking) compared to the Control group (36.0 lbs/milking). This increase in milk production was 2 lb more per milking at 4 and 5 months or at 76-121 days in milk of supplementation for the cows supplemented with Protein A compared with the Control cows (FIGS. 1, 2 and 6).

It is interesting to see the gradual increase in milk production (it does not show until the third month), followed by a sharp decrease in milk production once the product was removed 13 days before the last milk production record.

An analysis accounting for lame status in the model, revealed a tendency (P=0.06) for an interaction between treatment and lameness on milk yield. Interestingly, lame cows produced more (P<0.05) milk (37.7±0.89 lbs/milking) than sound cows (35.9±0.84 lbs/milking); but those on Control tended (P=0.06) to produce a bit less (36.5±1.02 lbs/milking; an increase of 1 lb/milking with respect to sound cows on Control) than those in the Protein A group (38.9 lbs/milking; an increase of 2.6 lbs/milking with respect to sound cows on Protein A). One could speculate that as milk production increased, lameness also increased, and that cows on Protein A, which produced more milk, suffered more lameness.

Figure 3:
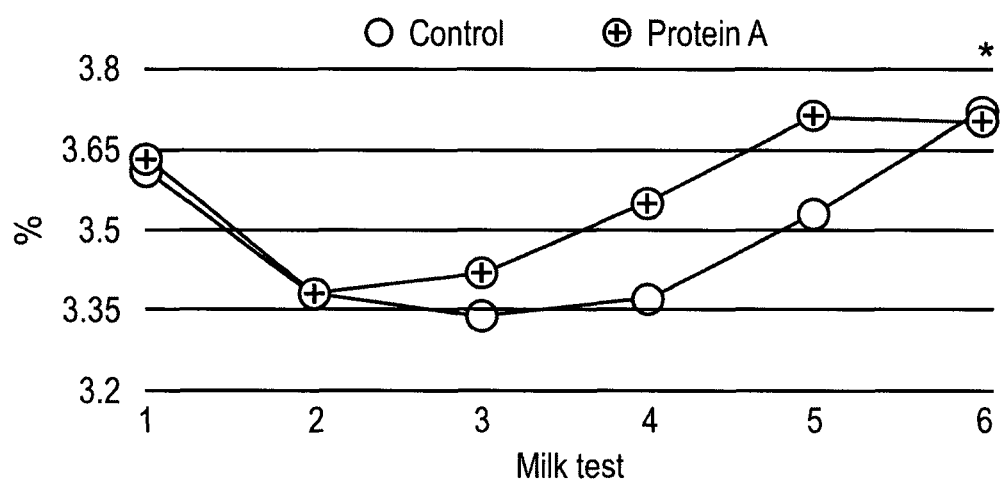
FIG. 3 is a graph plotting percent milk fat vs. milk test period (mos.). O=control diet; ⊗=SDP (Protein A) diet. In the $6^{th}$ tests, cows were on different treatments only for 17 days (the last 13 days before the test, all cows were on the same ration).
Figure 7:
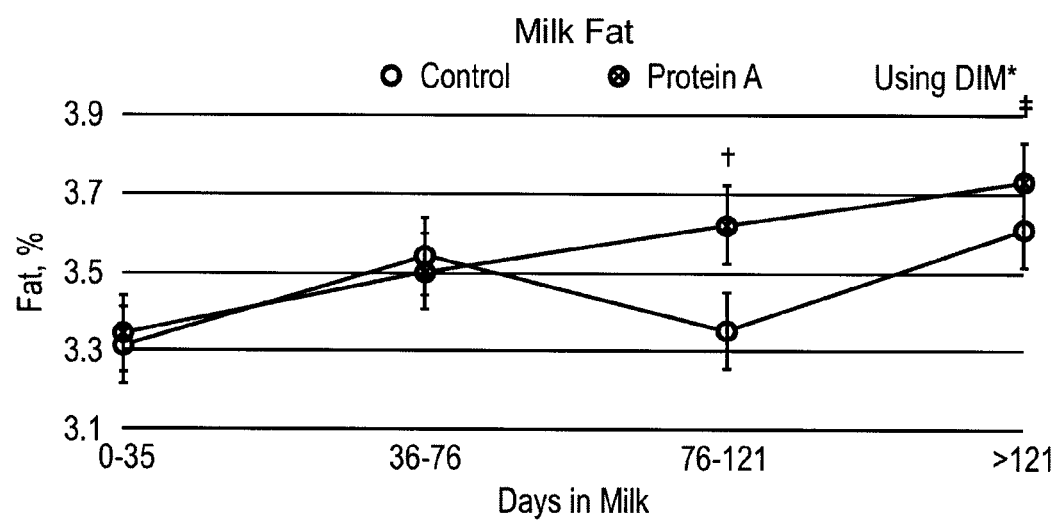
FIG. 7 is a graph plotting percent milk fat vs. periods of days in milk. O=control diet; ⊗=SDP (Protein A) Diet.

Milk fat was greater (P<0.05) in Protein A (3.55%) than in Control (3.47%). There was no interaction between treatment and time (P=0.18). The evolution of milk fat is depicted in FIG. 3 (months of supplementation) or FIG. 7 (Fat % vs. Days in milk).

Figure 8:
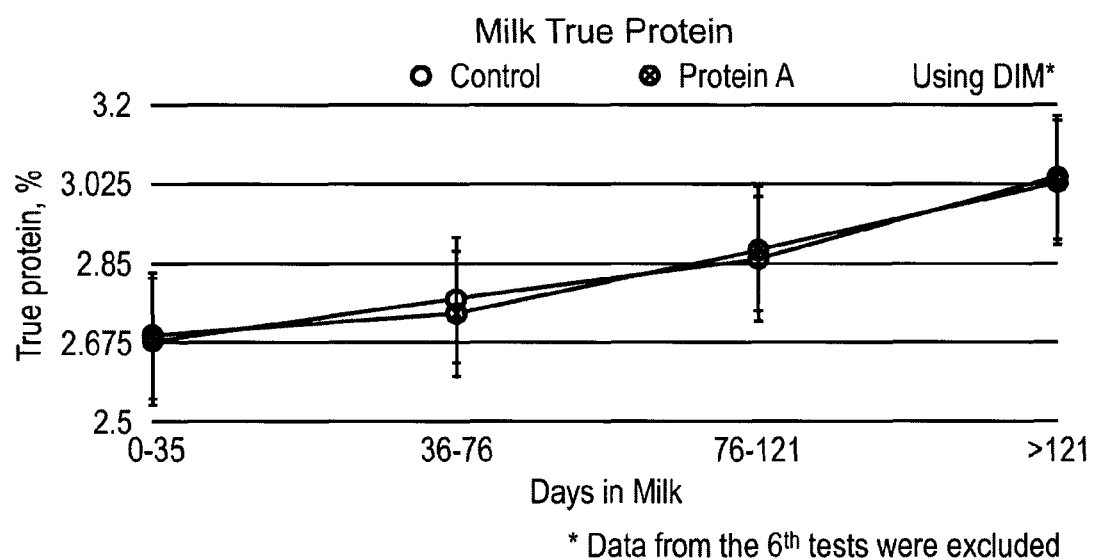
FIG. 8 is a graph plotting milk pure protein content vs. days in milk.

There were no differences (P=0.79) in milk true protein content between Control (2.84%) and Protein A (2.85%) nor in somatic cell count (P=0.99) between Control (3.83) and Protein A (3.82) cows (FIG. 8).

Contrary to the observations between milk yield and lameness, there were no interactions between treatment and lameness on milk protein and fat contents. There were no differences (P=0.99) in milk somatic cell counts between Control (3.83 ln) and Protein A (3.82 ln).

At the end of the study, out of the 473 cows on Control, 235 were pregnant (49.7%) and out of the 475 cows on Protein A, 223 (46.9%) were pregnant, but this difference was not significant (P=0.74).

Overall conception rate (number of pregnancies/number of services) was 22.8% and 19.4% for Control and Protein A cows, respectively, again, with this difference not being significant (P=0.16). Similarly, days at which pregnancy occurred were similar (P=0.24) between Control (97.2 d) and Protein A cows (92.5 d).

Body condition score (BCS) was not different between the two groups of cows at any of the times recorded. At calving, BCS was 3.0±0.03 and 3.0±0.03 for Control and Protein A, at 14 DIM it was 3.1±0.02 and 3.0±0.02 for Control and Protein A, and at 30 DIM it was 2.7±0.06 and 2.7±0.06 for Control and Protein A, respectively.

Blood concentration of BHBA at 5 DIM was 0.90±0.04 for Control and 0.92±0.04 for Protein A cows, again with no significant effects being observed (P=0.80).

Conclusions

Protein A had no effect on the incidence of metritis, retained placenta, DA, mastitis and culling and abortion rates. However, cows on Protein A tended to have a greater incidence of lameness. Milk yield and milk fat content were increased by. Protein A supplementation. Despite the increased milk yield and a tendency for greater lameness, reproductive parameters were not affected by Protein A.

Example 2

Four replications of Tilley-Terry incubations, each using 3 different rumen liquids from three rumen-cannulated cows were conducted to assess rumen fermentation and microbial changes, compared to an unsupplemented Control, induced by:

Spray-dried plasma (SDP) (Appetein®)
Spray-dried high hydrolyzed hemoglobin (SDHHH)
Urea 98% (Urea)
Soya
Yeast XPLS #151010 (Yeast)
Spray-dried red blood cells (SDRBC)

Rumen liquids were diluted to 10:40 and were supplemented (including the control) with 1% corn meal. All protein sources were supplemented to provide 2% N.

Incubations lasted 16 h, under continuous shaking (150 rpm), 5% $CO_2$ and 39° C.:

Sampling:

Concentrations of Gram negative and Gram positive bacteria were measured.

Results

The use of plasma proteins (SDP) has no effect on change in pH in the rumen of dairy cows.

Figure 4:
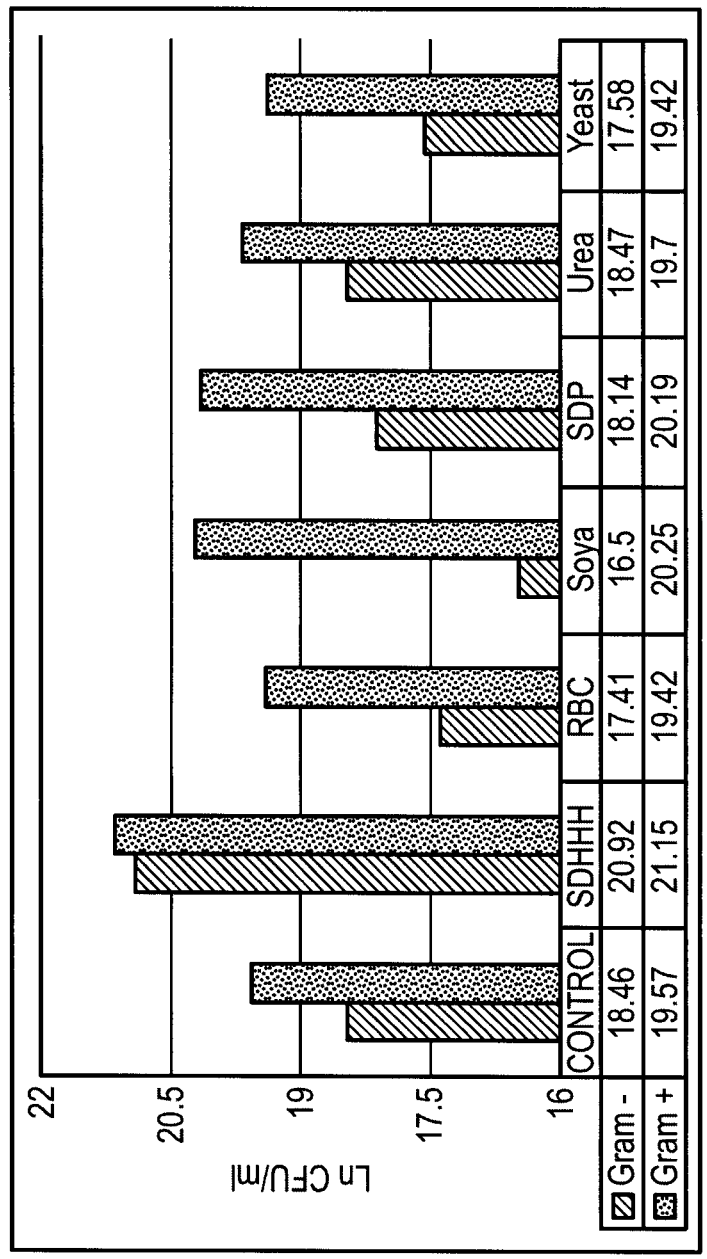
FIG. 4 is a graph of Ln bacterial CFU per mL for the control diet and 6 diets using other supplements.
Figure 5:
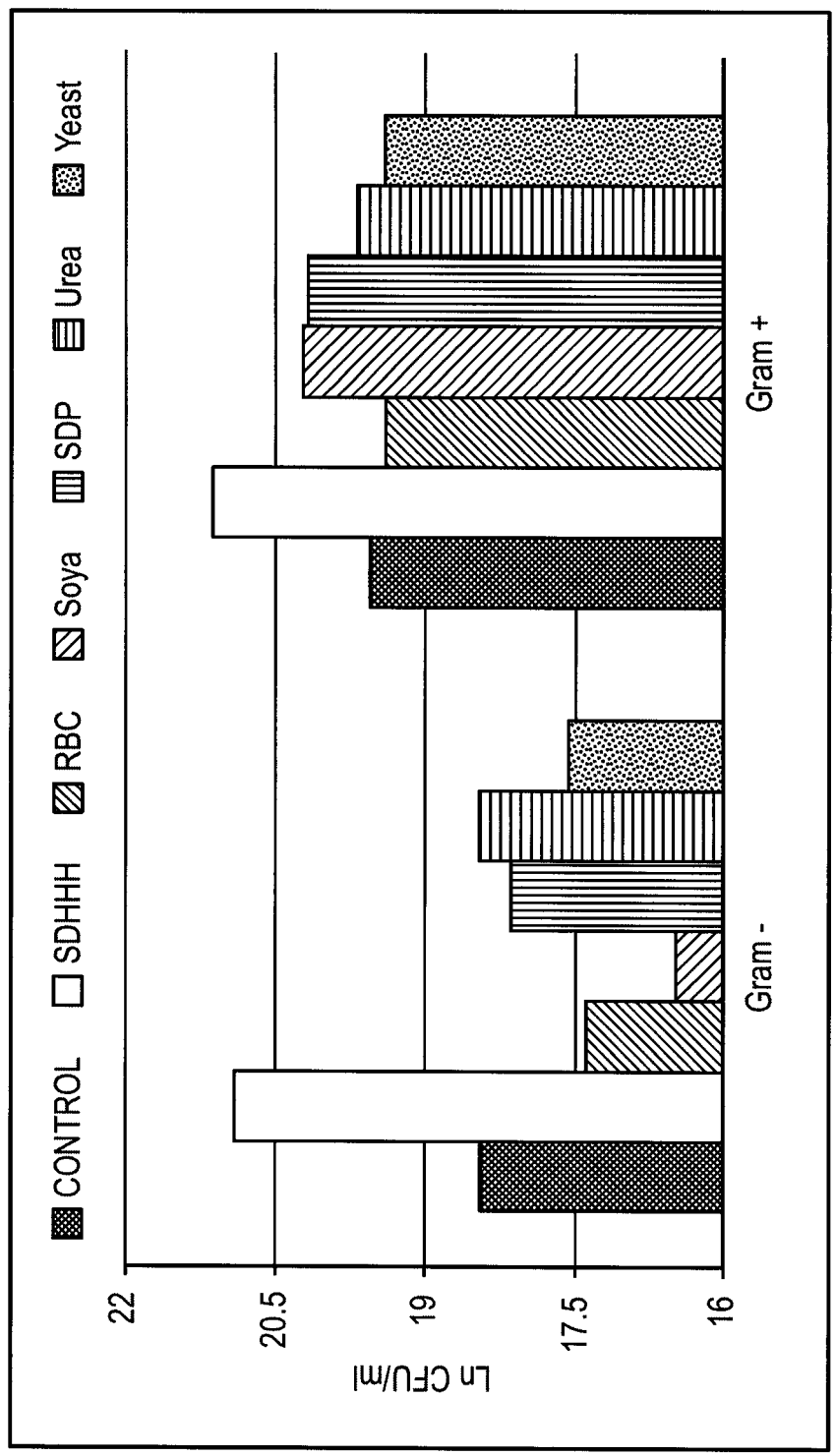
FIG. 5 is a graph plotting Ln CFU/mL of gram ⊖ and ⊕ bacteria for the control diet and 6 supplements.

SDHHH, a hydrolyzed product, had positive effects on increased rumen pH as happened with Yeast, Soya and plasma proteins (SDP), however spray dried plasma protein had no effect on growth of Gram− and Gram+ rumen bacteria compared with the control treatment, as shown in FIGS. 4 and 5. The hydrolyzed product had an increase in Gram+ bacteria indicating that this protein was degraded in the rumen. The results indicated that plasma proteins are not degraded by rumen bacteria and pass to the intestine as partially undegraded protein or by-pass protein, similar to spray-dried red blood cells, a well known by-pass protein used in the dairy industry.

The patents, patent applications and publications cited herein are incorporated by reference herein as though fully set forth.

REFERENCES

Borg, B. S., Campbell J. M., Koehnk H., Russell L. E., Thomson D. U., and Weaver E. M. 1999. Effects of a water soluble plasma protein product on weanling pig performance and health with and without *Escherichia coli* challenge. *Proceedings of Allen D. Leman Swine Conference* 26:23-24.

Chandler, P. T. 1991. Quantitative and qualitative characteristics of protein sources and interrelationships with energy. Virginia Dairyman 12:10, 12.

Clark, J. H., T. H. Klusmeyer, and M. A. Cameron. 1992. Microbial protein synthesis and flows of nitrogen fractions to the duodenum of dairy cows. J. Dairy Sci. 75:2304-2323.

Coffey, R. D., and Cromwell G. L. 2001. Use of spray-dried animal plasma in diets for weanling pigs. *Pig News Info.* 22:39N-48N.

Crenshaw et al., 2007. Lactation feed disappearance and wean to estrus interval for sows fed spray-dried plasma. J. Anim. Sci. 85:3442-3453.

Crenshaw et al., 2008. Effect of spray-dried plasma in diets fed to lactating sows on litter weight at weaning and subsequent farrowing rate. Proc. Allen D. Leman Swine Conf., Univ. MN, St. Paul, Minn., p 47.

Crenshaw et al., 2010. Effect of spray-dried plasma fed during gestation on pig performance at weaning. Proc. Allen D. Leman Swine Conf. Recent Res. Suppl., Univ. MN, St. Paul, Minn., p 193.

Dohoo et al., Can. J. Vet. Med., 67, 241-264 (2003)

National Research Council. 1985. Ruminant Nitrogen Usage. Natl. Acad. Sci., Washington, D.C.

National Research Council. 1989. Nutrient Requirements of Dairy Cattle. 6th rev. ed. Natl. Acad. Sci., Washington, D.C.

Safranski et al., 2010. Physiological and reproductive response to periparturient heat stress in sows. J. Anim. Sci. 89 (E-Suppl. 2):70.

Santos, F. A. P., J. T. Huber, C. B. Theurer, R. S. Swingle, J. M. Simas, K. H. Chen, and P. Yu. 1998. Milk yield and composition of lactating cows fed steam-flaked sorghum and graded levels of ruminally degradable protein. J. Dairy Sci. 81:215-220.

Santos, F. A. P, Santos, J. E. P., Theurer C. B., and J. T. Huber. 1998. Effects of rumen-undegradable protein on dairy cow performance: a 12-year literature review. J Dairy Sci 81:3182-3213.

Schingoethe, D. J. 1991. Protein quality and amino acid supplementation in dairy cattle. Pages 101-106 in Proc. Southwest Nutr. Manage. Conf., Tempe, Ariz. Dep. Anim. Sci., Univ. Arizona, Tucson.

Schor, A and G. A. Gagliostro. 2001. Undegradable protein supplementation to early-lactation dairy cows in grazing conditions J. Dairy Sci. 84:1597-1606.

Schwab, C. G. 1994. Optimizing amino acid nutrition for optimum yields of milk and milk protein. Pages 114-129 in Proc. Southwest Nutr. Manage. Conf., Phoenix, Ariz. Dep. Anim. Sci., Univ. Arizona, Tucson Song et al., 2012a. Effect of graded levels of dietary spray-dried plasma on pregnancy rate of mated female mice under transport stress as a model for stressed sows. J. Anim. Sci. Vol. 90 (E-Suppl. 2):112.

Song et al., 2012b. Effect of graded levels of dietary spray-dried plasma on growth and fetal characteristics of pregnant mice as a model for sows. J. Anim. Sci. Vol. 90 (E-Suppl. 2):112.

Spencer et al., 2003. Early weaning to reduce tissue mobilization in lactating sows and milk supplementation to enhance pig weaning weight during extreme heat stress. J. Anim. Sci. 81:2041-2052.

Schingoethe, D. J. 1991. Protein quality and amino acid supplementation in dairy cattle. Pages 101-106 in Proc. Southwest Nutr. Manage. Conf., Tempe, Ariz. Dep. Anim. Sci., Univ. Arizona, Tucson.

Torrallardona, D. 2010. Spray-dried animal plasma as an alternative to antibiotics in weanling pigs: a review. *Asian-Aust. J. Anim. Sci.* 32:131-148.

Van Dijk, A. J., Everts H., Nabuurs M. J. A., Margry R. J. C. F., and Beynen A. C. 2001. Growth performance of weanling pigs fed spray-dried animal plasma: a review. *Livest. Prod. Sci.* 68:263-274.

Van Iersel et al., 2011. Effect of spray-dried plasma in lactation feed on pig survival and litter weight at a commercial farm in Italy. Proc. Allen D. Leman Swine Conf., Recent Research Reports, College of Veterinary Medicine, Univ. MN, St. Paul, Minn., Vol. 38, p 281.

Virtanen, A. 1.1966. Milk production of cows on protein-free feeds. Science 153:1603-1608.

APPENDIX A

Abbreviations

SDP—Spray-Dried Animal Blood Plasma ("Protein A")
CP—Crude Protein
RDP—Rumen degradable protein
RUP—Rumen Undegradable Protein/Bypass Protein
SBM—Soy Bean Meal
EAA—Essential Amino Acids (AA)
SI—Small Intestine
FM—Fish Meal
MBM—Meat and bone meal
FtM—Feather Meal
BM—Blood Meal
CGM—Corn Gluten Meal
DDG—Distillers Dry Grains
DDGS—Distillers Dry Grains with Solubles
BDG—Brewers Dried Grains
BWG—Brewers Wet Grains
DM—Dry Matter DMI—Dry Matter Intake
DIM—Days in Milk (from last day of calving)
BCS—Body Condition Score
NFI—Non-Fiber Carbohydrate
TMR—Total Mixed Ration
BHBA—Beta-hydroxybutyric acid
SoyChlor—Acid Treated SBM
CIDR—Controlled Internal Drug Release
AI—Artificial Insemination
GnRH—Gonadotropin Releasing Hormone Having described the invention with reference to particular compositions and methods, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

The publications, including the patents and patent documents cited herein are incorporated by reference herein as though fully set forth.

What is claimed is:

1. A method for increasing milk production in a ruminant comprising feeding the ruminant an effective amount of an immunoglobulin source derived from the blood plasma or blood serum of an animal.

2. A method for increasing milk production in a ruminant comprising feeding an effective amount of an immunoglobulin source to the ruminant comprising a mixture of dried animal plasma, dried animal serum and dried animal immunoglobulin concentrate.

3. A method according to claim 1 or 2 that provides an amount of said immunoglobulin source that is about to 0.1 wt-%-10 wt-% of the total mixed ration (TMR) of the ruminant.

4. The method of claim 3 wherein the amount is about 1 wt-%-5 wt-% of the total mixed ration (TMR) of the ruminant.

5. The method according claim 1 or 2, wherein the ruminant is selected from the group consisting of a cow, sheep, goat, horse, yak, camel and llama.

6. The method of claim 5 wherein the ruminant is a cow.

7. The method according to claim 1 or 2 wherein said immunoglobulin source is derived from pigs, cattle, sheep, horses and poultry.

8. The method according to claim 1 or 2 that also increases milk fat content of the milk.

9. The method of claim 1 or 2 that maintains reproductive parameters in a cow, sheep, goat, horse, yak, camel or llama, wherein the reproductive parameter is selected from the group consisting of pregnancy rate and conception rate.

10. The method of claim 1 or 2 that maintains or improves body score condition in a cow, sheep, goat, horse, yak, camel or llama.

11. The method of claim 10 wherein the ruminant is a dairy cow.

12. The method of claim 1 or 2 whereby the immunoglobulin source is obtained in dried form from animal plasma or animal serum by spray-drying, freeze drying, ring drying or flash drying.

13. The method of claim 1 or 2 wherein the immunoglobulin source is administered in liquid form.

* * * * *